(12) United States Patent
Chung et al.

(10) Patent No.: US 8,410,328 B2
(45) Date of Patent: *Apr. 2, 2013

(54) METHOD OF PREPARING MULTICOMPONENT BISMUTH MOLYBDATE CATALYSTS COMPRISING FOUR METAL COMPONENTS AND METHOD OF PREPARING 1,3-BUTADIENE USING SAID CATALYSTS

(75) Inventors: Young Min Chung, Daejeon (KR); Tae Jin Kim, Daejeon (KR); Seong Jun Lee, Daejeon (KR); Yong Seung Kim, Daejeon (KR); Seung Hoon Oh, Seoul (KR); In Kyu Song, Seoul (KR); Hee Soo Kim, Seoul (KR); Ji Chul Jung, Seoul (KR); Ho Won Lee, Seoul (KR)

(73) Assignees: SK Innovation Co., Ltd., Seoul (KR); SK Global Chemical Co., Ltd., Seoul (KR)

(*) Notice: Subject to any disclaimer, the term of this patent is extended or adjusted under 35 U.S.C. 154(b) by 334 days.

This patent is subject to a terminal disclaimer.

(21) Appl. No.: 12/733,865

(22) PCT Filed: Aug. 24, 2008

(86) PCT No.: PCT/KR2008/004991
§ 371 (c)(1),
(2), (4) Date: Mar. 23, 2010

(87) PCT Pub. No.: WO2009/044999
PCT Pub. Date: Apr. 9, 2009

(65) Prior Publication Data
US 2010/0249482 A1  Sep. 30, 2010

(51) Int. Cl.
*C07C 5/48* (2006.01)
*B01J 23/31* (2006.01)

(52) U.S. Cl. ........ 585/626; 585/601; 585/616; 585/617; 585/621; 585/624; 502/305; 502/306; 502/311; 502/315; 502/316; 502/353

(58) Field of Classification Search .......... 502/305, 502/311, 353, 306, 315, 316; 585/601, 616, 585/617, 621, 624, 626
See application file for complete search history.

(56) References Cited

U.S. PATENT DOCUMENTS

| | | | | |
|---|---|---|---|---|
| 3,414,631 A | * | 12/1968 | Grasselli et al. | 585/622 |
| 3,764,632 A | | 10/1973 | Takenaka et al. | |
| 3,895,049 A | * | 7/1975 | Umemura et al. | 558/324 |
| 3,956,181 A | * | 5/1976 | Grasselli et al. | 502/212 |
| 3,966,823 A | * | 6/1976 | Takenaka et al. | 568/479 |

(Continued)

OTHER PUBLICATIONS

Soares, et al., "Synergy Effects Between β and γ Phases of Bismuth Molybdates in the Selective Catalytic Oxidation of 1-Butene" in Applied Catalysis A: General 253 (2003), 191-200—2003, month unknown.*

(Continued)

*Primary Examiner* — In Suk Bullock
*Assistant Examiner* — Bradley Etherton
(74) *Attorney, Agent, or Firm* — Abelman, Frayne & Schwab (57) ABSTRACT

A method of preparing multicomponent bismuth molybdate catalysts composed of four metal components and a method of preparing 1,3-butadiene using the catalyst, and particularly, to multicomponent bismuth molybdate catalysts composed of a divalent cationic metal, a trivalent cationic metal, bismuth and molybdenum, a preparation method thereof, and a method of preparing 1,3-butadiene from a C4 mixture including n-butene and n-butane using oxidative dehydrogenation are described.

8 Claims, 3 Drawing Sheets

U.S. PATENT DOCUMENTS 3,972,954 A * 8/1976 Bertus .................... 585/622
3,998,867 A   12/1976 Takenaka et al.
4,547,615 A * 10/1985 Yamamoto ............... 585/621

OTHER PUBLICATIONS

M.A. Chaar et al.; "Selective Oxidative Dehydrogenation of Propane over V-Mg-O Catalysts"; Journal of Catalysis 109, 463-467 (1998).

E.A. Mamedov et al.; "Oxidative dehydrogenation of lower alkanes on vanadium oxide-based catalysts. The present state of the art and outlooks"; Elsevier Science B.V; Applied Catalysis A: General 127 (1995) 1-40.

Madeira et al.; "Catalytic Oxidative Dehydrogenation of n-Butane"; Catalysis Reviews; 44(2), 247-286 (2002).

Rennard et al.; "Oxidative Dehydrogenation of Butenes over Ferrite Catalysts"; Journal of Catalysis 21, 282-293 (1971).

Cares et al.; "Ferrite Spinels as Catalysts in the Oxidative Dehydrogenation of Butenes"; Journal of Catalysis 23, 193-203 (1971).

Gibson et al.; Oxidative Dehydrogenation of Butenes over Magnesium Ferrite Kinetic and Mechanistic Studies; Journal of Catalysis 41, 420-430 (1976).

Kung et al.; "Selective Oxidative Dehydrogenation of Butenes on Ferrite Catalysts"; Advances in Catalysis, vol. 33; 159-198 (1985).

Toledo et al.; Oxidative dehydrogenation of 1-butene to butadiene on $\alpha$-Fe2O3/ZnAl2O4 and ZnFexAl2-xO4 catalysts; Catalysis Letters 30 (1995) 279-288.

Bakshi et al; "Catalytic Properties of System SnO2:Sb2O4 in the Oxidative Dehydrogenation of n-Butenes to Butadiene"; Petroleum Chemistry U.S.S.R., vol. 7, 177-185 (1967).

Bleijenberg et al.; "Catalytic Oxidation of 1-Butene over Bismuth Molybdate Catalysts"; Journal of Catalysis 4, 581-585 (1965).

Batist et al.; "The Catalytic Oxidation of 1-Butene over Bismuth Molybdate Catalysts"; Journal of Catalysis 5, 55-64 (1966).

Wolfs et al.; "The Selective Oxidation of 1-Butene Over a Multicomponent Molybdate Catalyst. Influences of Various Elements on Structure and Activity"; Journal of Catalysts 32, 25-36 (1974).

Linn et al.; "Oxidation of 1-Butene over Bismuth Molybdates and Bismuth Iron Molybdate"; Journal of Catalysis 41, 134-139 (1976).

Ueda et al.; "Catalytic Properties of Tricomponent Metal Oxides Having the Scheelite Structure"; Journal of Catalysis 101, 360-368 (1986).

Yoshihiko Moro-Oka et al.; "Multicomponent Bismuth Molybdate Catalyst: A Highly Functionalized Catalyst System for the Selective Oxidation of Olefin"; Advances in Catalysts, vol. 40; 233-273 (1994).

R.K. Grasselli; "Ammoxidation"; Organic Reactions; Handbook of Heterogeneous Catalysis, vol. 5, 2302-2326 (1997).

B. Grzybowska et al.; "The Chemistry of Bi-Mo Oxide Catalysts"; Journal of Catalysis 25, 25-32 (1972).

Soares; "Synergy effect between $\beta$ and $\gamma$ phases of bismuth molybdates in the selective catalytic oxidation of 1-butene"; Elsevier; Applied Catalysis A: General 253 (2003) 191-200.

* cited by examiner

METHOD OF PREPARING MULTICOMPONENT BISMUTH MOLYBDATE CATALYSTS COMPRISING FOUR METAL COMPONENTS AND METHOD OF PREPARING 1,3-BUTADIENE USING SAID CATALYSTS

CROSS-REFERENCE TO RELATED APPLICATIONS

This application is a National Phase of PCT/KR2008/004991, filed 24 Aug., 2008, which claims priority from Korean Application Number 102007 0099345, filed 2 Oct. 2007.

TECHNICAL FIELD

The present invention relates to a method of preparing multicomponent bismuth molybdate catalysts having a simple composition of four metal components and a method of preparing 1,3-butadiene using the catalyst, and more particularly, to a method of preparing a multicomponent bismuth molybdate catalyst comprising a divalent cationic metal, a trivalent cationic metal, bismuth, and molybdenum and to a method of preparing high value-added 1,3-butadiene from an inexpensive C4 mixture including n-butene and n-butane, without utilization of an additional process for removing n-butane or separating n-butene, over the above catalyst, in which the multicomponent bismuth molybdate catalyst having high activity for the inventive reaction can be prepared only using four metal components, this being arrived at through systematic investigation of the types and ratios of metal components, thus simplifying the synthesis route and composition of the catalyst, thereby ensuring reproducibility of catalyst preparation, and also, 1,3-butadiene can be produced at high yield using the above catalyst.

BACKGROUND ART 1,3-butadiene, the demand for and value of which is gradually increasing as pertains to its use as an intermediate of many petrochemical products in petrochemical markets, is prepared using naphtha cracking, the direct dehydrogenation of n-butene, and the oxidative dehydrogenation of n-butene. However, the naphtha cracking process, which is responsible for 90% or more of 1,3-butadiene supplied to the markets, entails high energy consumption due to high reaction temperatures, and as well, is not a single process for producing 1,3-butadiene, and undesirably produces other fractions in surplus in addition to the 1,3-butadiene. Accordingly, this process is disadvantageous because investment in and management of a naphtha cracker cannot be optimized to satisfy the production demand for 1,3-butadiene, and thus, even though more novel naphtha crackers be utilized, the increasing demand for butadiene cannot be effectively satisfied. In addition, the direct dehydrogenation of n-butene is thermodynamically disadvantageous and is also unsuitable for commercial production of 1,3-butadiene because it is an endothermic reaction and thus requires high-temperature and low-pressure conditions to produce 1,3-butadiene at high yield [M. A. Chaar, D. Patel, H. H. Kung, J. Catal., vol. 109, pp. 463 (1988)/E. A. Mamedov, V. C. Corberan, Appl. Catal. A, vol. 127, pp. 1 (1995)/L. M. Madeira, M. F. Portela, Catal. Rev., vol. 44, pp. 247 (2002)].

In addition, the oxidative dehydrogenation of n-butene is a reaction for producing 1,3-butadiene through removal of two hydrogens from n-butene using oxygen as a reactant, and is thermodynamically advantageous because water, which is stable, is produced. Further, this process is commercially advantageous because 1,3-butadiene may be obtained at high yield even at lower reaction temperatures than direct dehydrogenation, without the need to additionally apply heat, thanks to exothermic properties. Furthermore, this process produces not only 1,3-butadiene but also water and therefore manifests energy reduction effects including additional production of steam. Hence, the oxidative dehydrogenation of n-butene for the production of 1,3-butadiene may be effective as a single production process able to satisfy the increasing demand for 1,3-butadiene. In particular, when a C4 raffinate-3 or C4 mixture including impurities, such as n-butane, used as an n-butene source, is directly used as a reactant without utilization of an additional process for separating n-butene, an advantage of adding high value to the C4 fractions produced in surplus may be realized. Specifically, the C4 raffinate-3 mixture, which is the reactant used in the present invention, is an inexpensive C4 fraction remaining after the separation of useful compounds, including 1,3-butadiene, isobutylene, 1-butene, etc., from a C4 mixture produced through naphtha cracking. More specifically, a first mixture remaining after extracting 1,3-butadiene from a C4 mixture produced through naphtha cracking is called raffinate-1, a second mixture remaining after extracting isobutylene from the raffinate-1 is called raffinate-2, and a third mixture remaining after extracting 1-butene from the raffinate-2 is called raffinate-3. Therefore, the C4 raffinate-3 is composed mainly of 2-butene (trans-2-butene and cis-2-butene), n-butane, and residual 1-butene.

According to the oxidative dehydrogenation of n-butene (1-butene, trans-2-butene, cis-2-butene) as mentioned above, n-butene reacts with oxygen, thus producing 1,3-butadiene and water. Although the oxidative dehydrogenation of n-butene has many advantages as a commercial process, it suffers because oxygen is used as the reactant in the above reaction, undesirably causing many side-reactions, including complete oxidation, etc. Thus, in order to efficiently improve the catalyst process, the development of catalysts having high selectivity for 1,3-butadiene while retaining high activity through control of the oxidation capability of the catalyst is of utmost importance. Examples of the catalysts known to date for use in the oxidative dehydrogenation of n-butene include ferrite-based catalysts [R. J. Rennard, W. L. Kehl, J. Catal., vol. 21, pp. 282 (1971)/W. R. Cares, J. W. Hightower, J. Catal., vol. 23, pp. 193 (1971)/M. A. Gibson, J. W. Hightower, J. Catal., vol. 41, pp. 420 (1976)/H. H. Kung, M. C. Kung, Adv. Catal., vol. 33, pp. 159 (1985)/J. A. Toledo, M. A. Valenzuela, H. Annendariz, G. Aguilar-Rios, Zapzta, A. Montoya, N. Nava, P. Salas, I. Schiffer, Catal. Lett., vol. 30, pp. 279 (1995)], tin-based catalysts [Y. M. Bakshi, R. N. Gur'yanova, A. N. Mal'yan, A. I. Gel'bshtein, Petroleum Chemistry U.S.S.R., vol. 7, pp. 177 (1967)], and bismuth molybdate-based catalysts [A. C. A. M. Bleijenberg, B. C. Lippens, G. C. A. Schuit, J. Catal., vol. 4, pp. 581 (1965)/Ph. A. Batist, B. C. Lippens, G. C. A. Schuit, J. Catal., vol. 5, pp. 55 (1966)/M. W. J. Wolfs, Ph. A. Batist, J. Catal., vol. 32, pp. 25 (1974)/W. J. Linn, A. W. Sleight, J. Catal., vol. 41, pp. 134 (1976)/W. Ueda, K. Asakawa, C.-L. Chen, Y. Moro-oka, T. Ikawa, J. Catal., vol. 101, pp. 360 (1986)/Y. Moro-oka, W. Ueda, Adv. Catal., vol. 40, pp. 233 (1994)/R. K. Grasselli, Handbook of Heterogeneous Catalysis, vol. 5, pp. 2302 (1997)].

Among these catalysts, the bismuth molybdate-based catalyst includes pure bismuth molybdate catalysts comprising bismuth and molybdenum oxide and multicomponent bismuth molybdate catalysts further comprising various metal components. Pure bismuth molybdate is present in various phases, and, in particular, three phases including α-bismuth molybdate ($Bi_2Mo_3O_{12}$), β-bismuth molybdate ($Bi_2Mo_2O_9$) and γ-bismuth molybdate ($Bi_2MoO_6$) are known to be useful as catalysts [B. Grzybowska, J. Haber, J. Komorek, J. Catal., vol. 25, pp. 25 (1972)/A. P. V. Soares, L. K. Kimitrov, M. C. A. Oliveira, L. Hilaire, M. F. Portela, R. K. Grasselli, Appl. Catal. A, vol. 253, pp. 191 (2003)]. However, a process of preparing 1,3-butadiene through the oxidative dehydrogenation of n-butene over a pure bismuth molybdate catalyst is limited in increasing the yield of 1,3-butadiene and is thus unsuitable for use as a commercial process [Y. Moro-oka, W. Ueda, Adv. Catal., vol. 40, pp. 233 (1994)]. As an alternative thereto, in order to increase the activity of the bismuth molybdate catalyst for the oxidative dehydrogenation of n-butene, attempts to prepare multicomponent bismuth molybdate catalysts comprising not only bismuth and molybdate but also other metal components have been made [M. W. J. Wolfs, Ph. A. Batist, J. Catal., vol. 32, pp. 25 (1974)/S. Takenaka, A. Iwamoto, U.S. Pat. No. 3,764,632 (1973)].

Some patents and literature have reported multicomponent bismuth molybdate catalysts for the oxidative dehydrogenation of n-butene. Specifically, many reports have been made of the oxidative dehydrogenation of 1-butene at 520° C. using a mixed oxide catalyst composed of nickel, cesium, bismuth, and molybdenum, resulting in 1,3-butadiene at a yield of 69% [M. W. J. Wolfs, Ph. A. Batist, J. Catal., vol. 32, pp. 25 (1974)], of the oxidative dehydrogenation of a C4-mixture including n-butane and n-butene at 470° C. using a mixed oxide catalyst composed of cobalt, iron, bismuth, magnesium, potassium, and molybdenum, resulting in 1,3-butadiene at a maximum yield of 62% [S. Takenaka, H. Shimizu, A. Iwamoto, Y. Kuroda, U.S. Pat. No. 3,998,867 (1976)], and of the oxidative dehydrogenation of 1-butene at 320° C. using a mixed oxide catalyst composed of nickel, cobalt, iron, bismuth, phosphorus, potassium, and molybdenum, resulting in 1,3-butadiene at a maximum yield of 96% [S. Takenaka, A. Iwamoto, U.S. Pat. No. 3,764,632 (1973)].

In the process for preparing 1,3-butadiene using the multicomponent bismuth molybdate catalyst disclosed in the above literature, 1,3-butadiene may be obtained at high yield when n-butene, in particular, 1-butene having relatively high reaction activity, is used alone as the reactant. In the case where a C4 mixture including n-butane and n-butene is used as a reactant, a multicomponent bismuth molybdate catalyst having a complicated composition of six or more metal components at a predetermined ratio should be used. That is, additional metal components must be continuously added to increase the activity of the catalyst, and thus the catalyst has a very complicated composition, undesirably resulting in a complicated catalyst synthesis route and a difficulty in ensuring reproducibility of catalyst preparation. In the above conventional techniques, as the reactant, only pure n-butene (1-butene or 2-butene) is used, or otherwise, a C4 mixture including n-butane and n-butene but having low n-butane content of less than 10 wt % is used. In the case where a C4 mixture having high n-butane content is used as the reactant, the yield of 1,3-butadiene is lowered. Because the C4 mixture which is easily obtainable as a result of actual petrochemical processes has high n-butane content, in order to apply the conventional catalyst to a commercial process, there is a need for an additional process for separating n-butene, inevitably remarkably decreasing economic efficiency. As a typical example, in a commercial process using a ferrite catalyst, a C4 mixture in which the n-butane content is maintained as low as less than 5 wt % is used as the reactant.

As mentioned above, the literature and patents regarding the catalyst and process for preparing 1,3-butadiene through the oxidative dehydrogenation of n-butene are characterized in that 1,3-butadiene may be obtained at high yield when using pure 1-butene or 2-butene as the reactant, and further, in the case where a C4 mixture having very high n-butene content is used as the reactant, a multicomponent bismuth molybdate catalyst having a very complicated combination of many metal components to increase the activity of the catalyst should be used, thus complicating the catalyst synthesis route and deteriorating the reproducibility of catalyst preparation. However, cases in which 1,3-butadiene is prepared from C4 fractions including C4 raffinate-3 or a C4 mixture having high n-butane content over a multicomponent bismuth molybdate catalyst having a simple composition of four metal components have not yet been reported.

DISCLOSURE

Technical Problem

Leading to the present invention, intensive and thorough research carried out by the present inventors aiming to solve the problems encountered in the prior art, led to the development of multicomponent bismuth molybdate catalysts composed exclusively of four metal components showing superior reproducibility of catalyst preparation through the appropriate selection of the types of metal components and the adjustment of the ratios of metal components in catalysts, the catalysts having high activity for the oxidative dehydrogenation of n-butene, and also, resulted in the finding that, when an inexpensive C4 mixture having high n-butane content, which has not been subjected to an additional separation process, is used as a reactant over the above catalyst, 1,3-butadiene may be prepared at high yield through the oxidative dehydrogenation of n-butene.

Accordingly, the present invention provides a multicomponent bismuth molybdate catalyst for the production of 1,3-butadiene, which is composed exclusively of four metal components. In addition, the present invention provides a method of preparing the multicomponent bismuth molybdate catalyst having high activity for the inventive process by simply coprecipitating metal components at an appropriate ratio without specific control of factors used in catalyst preparation, including pH and temperature, in the course of coprecipitation of four metal components. In addition, the present invention provides a method of preparing 1,3-butadiene through the oxidative dehydrogenation of n-butene directly using as a reactant a C4 mixture which has not been subjected to an additional separation process, in the presence of the above catalyst.

Technical Solution

According to the present invention, multicomponent bismuth molybdate catalysts for the production of 1,3-butadiene have a simple composition of four metal components. The four metal components include a divalent cationic metal, a trivalent cationic metal, bismuth, and molybdenum. The technique for preparing multicomponent bismuth molybdate catalysts composed of four metal components, which is realized in the present invention, is characterized in that the catalyst is prepared only through coprecipitation of metal components without specific control of factors of catalyst preparation, thus simplifying the synthesis route, resulting in superior reproducibility of catalyst preparation.

According to the present invention, a method of preparing a multicomponent bismuth molybdate catalyst for use in the production of 1,3-butadiene may comprise a) preparing a first solution including a precursor of a trivalent cationic metal including iron, a precursor of a divalent cationic metal selected from among magnesium, manganese, cobalt, nickel, copper and zinc, and a bismuth precursor; b) preparing a second solution in which a molybdenum precursor is dissolved; c) adding the first solution in droplets to the second solution so that coprecipitation occurs, thus obtaining a coprecipitation solution; d) subjecting the coprecipitation solution to stirring for 1~2 hours and then dewatering, thus obtaining a solid component; and e) subjecting the solid component to drying at 150~200° C. and then thermal treatment at 400~600° C.

In addition, according to the present invention, a method of preparing 1,3-butadiene may comprise a) packing a reactor with a fixed bed of the bismuth molybdate catalyst prepared through any one of claims 1 to 5; b) performing oxidative dehydrogenation while continuously passing reactants comprising a C4 mixture including n-butene, air, and steam through the catalyst bed of the reactor; and c) obtaining 1,3-butadiene.

Advantageous Effects

According to the present invention, a multicomponent bismuth molybdate catalyst for use in the production of 1,3-butadiene can be prepared only using four metal components showing high activity for the oxidative dehydrogenation of n-butene as shown through systematic investigation of the types and ratios of metal components. Compared to conventional mixed oxide catalysts having a very complicated composition of many metal components, the catalyst according to the present invention is simple in terms of its composition and synthesis route and is favorable for ensuring reproducibility, and can thus be directly applied to a commercial process.

When the multicomponent bismuth molybdate catalyst composed of four metal components according to the present invention is used, it is possible to prepare 1,3-butadiene directly using as a reactant a C4 mixture having high n-butane content, without utilization of an additional process for removing n-butane or separating n-butene, through the oxidative dehydrogenation of n-butene in the C4 mixture.

According to the present invention, 1,3-butadiene having high use value can be directly prepared from a C4 mixture or C4 raffinate-3 which is useless in the petrochemical industries, thereby adding high value to the inexpensive C4 fraction. The catalyst process of the present invention is a single process for producing 1,3-butadiene unlike conventional 1,3-butadiene production through naphtha cracking, and thus can actively comply with changes in the demand for 1,3-butadiene.

BEST MODE

Hereinafter, a detailed description will be given of the present invention. As mentioned above, the present invention is directed to a method of preparing a multicomponent bismuth molybdate catalyst through coprecipitation using four metal components showing superior reproducibility of catalyst preparation thanks to the composition and synthesis route which is simpler than in conventional techniques, the catalyst having high activity for the oxidative dehydrogenation of n-butene. Also, a method of preparing 1,3-butadiene through the oxidative dehydrogenation of n-butene using the aforementioned catalyst is also provided, by which 1,3-butadiene can be produced at high yield from a C4 mixture having high n-butane content, which has not been subjected to an additional process for removing n-butane or separating n-butene.

Specifically, in the present invention, the C4 mixture indicates an inexpensive C4 raffinate-3 composed mainly of n-butane and n-butene remaining after separating useful compounds from a C4 mixture produced through naphtha cracking. Typically, a first mixture remaining after extracting 1,3-butadiene from the C4 mixture is called raffinate-1, a second mixture remaining after extracting isobutylene from the raffinate-1 is called raffinate-2, and a third mixture remaining after extracting 1-butene from the raffinate-2 is called raffinate-3. Thus, the C4 raffinate-3 serving as the reactant in the present invention is a C4 mixture, which is composed mainly of 2-butene (trans-2-butene and cis-2-butene), n-butane, and residual 1-butene.

The catalyst of the present invention for use in the production of 1,3-butadiene at high yield through the oxidative dehydrogenation of n-butene is a multicomponent bismuth molybdate catalyst composed of four metal components.

The activity of the multicomponent bismuth molybdate catalyst varies depending on the number of metal components and the ratio thereof. Unlike conventional mixed oxide catalysts having a very complicated composition of many metals, a multicomponent bismuth molybdate catalyst according to the present invention has a simple composition of four metal components showing high activity for the oxidative dehydrogenation of n-butene which is obtained through systematic investigation of the types of metal components and ratios thereof.

The multicomponent bismuth molybdate catalyst composed of four metal components includes a divalent cationic metal, a trivalent cationic metal, bismuth, and molybdenum. An example of the trivalent cationic metal includes iron which is reported in conventional literature to be greatly adapted for use in a multicomponent bismuth molybdate catalyst, and examples of the divalent cationic metal include magnesium, manganese, cobalt, nickel, copper, and zinc. Examples of the metal precursors for the preparation of the multicomponent bismuth molybdate catalyst include any metal precursors which are typically used in the art. In the present invention, useful are magnesium nitrate as the magnesium precursor, manganese nitrate as the manganese precursor, cobalt nitrate as the cobalt precursor, nickel nitrate as the nickel precursor, copper nitrate as the copper precursor, zinc nitrate as the zinc precursor, iron nitrate as the iron precursor, bismuth nitrate as the bismuth precursor, and ammonium molybdate as the molybdenum precursor. When the ratio of the metal precursors is variously altered, many multicomponent bismuth molybdate catalysts may be prepared. However, in the present invention, in order to increase the activity of the multicomponent bismuth molybdate catalyst composed of four metal components, the molar ratio of bismuth precursor:molybdenum precursor is adjusted to 1~10:5~20, and preferably 1:12, thereby preparing catalysts having high activity for the oxidative dehydrogenation of n-butene through the changes in the types and ratios of divalent and trivalent cationic metals.

The divalent cationic metal, the trivalent cationic metal, and the bismuth precursor are dissolved together in distilled water, whereas the molybdenum precursor is separately dissolved, also in distilled water. As such, depending on the type of precursor, an acid solution (e.g., nitric acid) may be added to increase the solubility thereof. Thereafter, the metal precursor mixture solution including the divalent cationic metal, the trivalent cationic metal, and the bismuth is added to the molybdenum precursor solution at a predetermined rate, thus coprecipitating metal components. The coprecipitated solution is stirred for 0.5~24 hours and preferably 1~2 hours to realize sufficient coprecipitation. Then, water and other liquid components are eliminated from the stirred solution using a vacuum concentrator or a centrifuge, thus obtaining a solid sample. The solid sample thus obtained is dried at 20~300° C., and preferably 150~200° C., for 24 hours. The solid catalyst thus produced is placed in an electrical furnace so that it is thermally treated at 300~800° C., preferably 400~600° C., and more preferably 450~500° C., thereby preparing a multicomponent bismuth molybdate catalyst.

Figure 1:
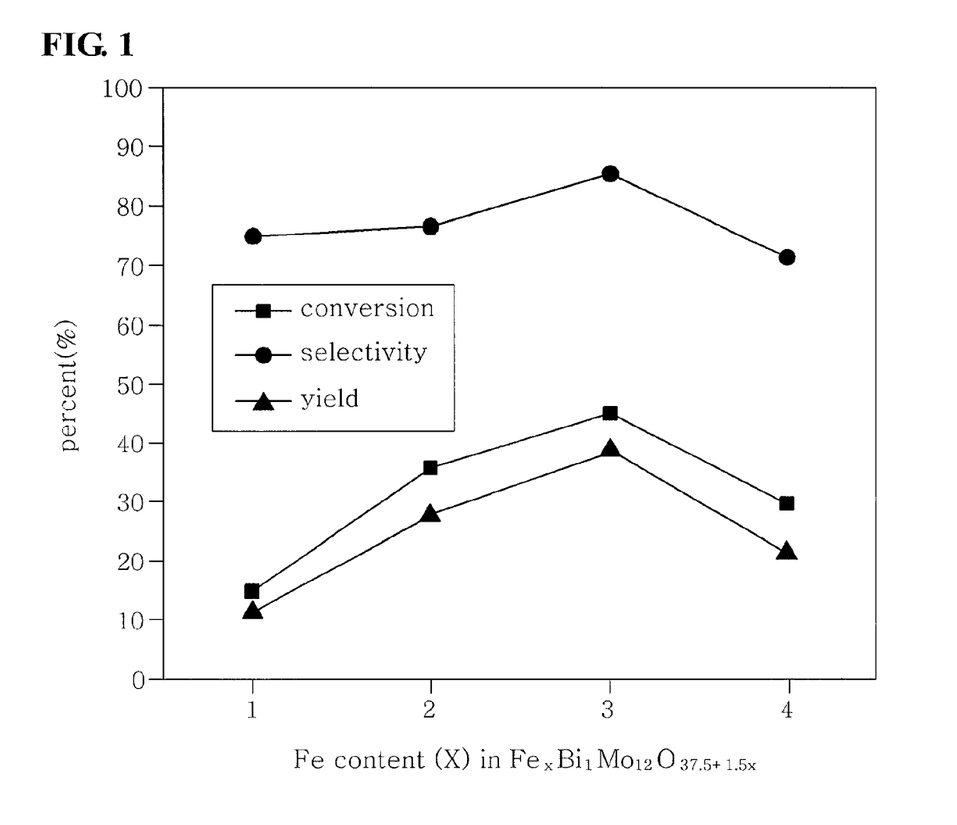
FIG. 1 is a graph showing the reaction activity of four multicomponent bismuth molybdate catalysts composed of three metal components depending on changes in the trivalent cationic iron (Fe) content, according to Example 1 of the present invention.

Specifically, with the goal of preparing a multicomponent bismuth molybdate catalyst composed of four metal components showing high activity for the oxidative dehydrogenation of n-butene, first, to fix the molar ratio of the trivalent cationic metal in the catalyst, a multicomponent bismuth molybdate catalyst composed of three metal components with the exception of a divalent cationic metal is prepared according to a preparative example of the present invention. As such, as the trivalent cationic metal, using iron which is known to be the most preferable as a trivalent cationic metal in multicomponent bismuth molybdate catalysts as mentioned above, the activity of the catalyst for the oxidative dehydrogenation of n-butene is determined depending on changes in the iron content in the catalyst. As a result thereof, the molar ratio of iron:bismuth:molybdenum is fixed to 2~4: 1:5~20, and preferably 3:1:12 (FIG. 1).

Figure 2:
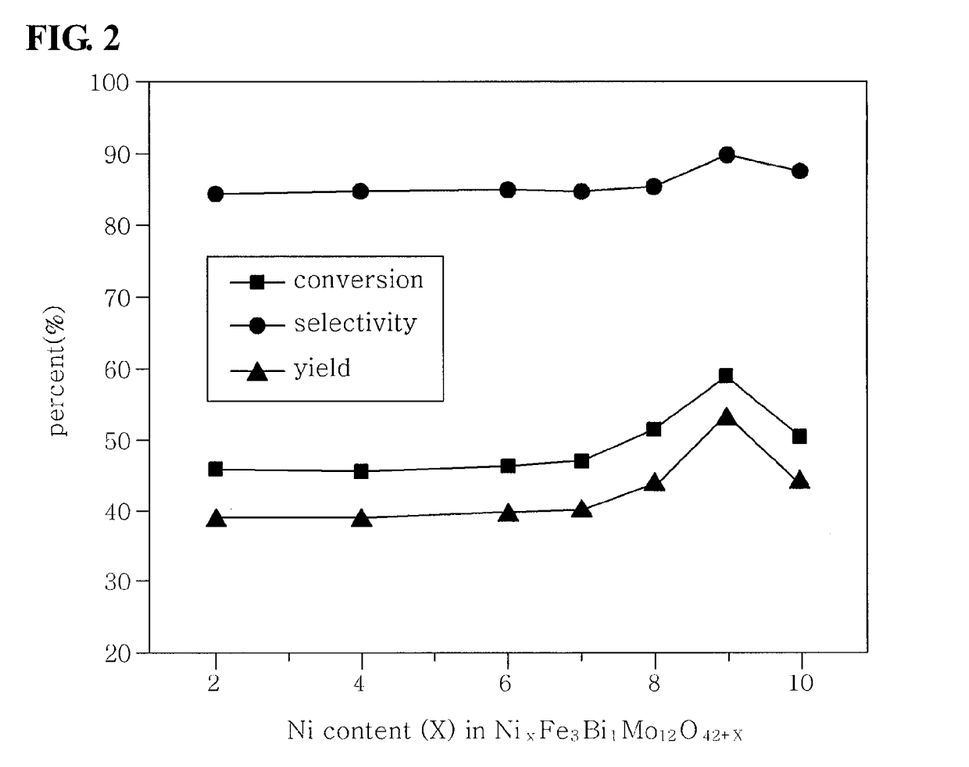
FIG. 2 is a graph showing the reaction activity of seven multicomponent bismuth molybdate catalysts composed of four metal components depending on changes in the divalent cationic nickel (Ni) content, according to Example 2 of the present invention.

In addition, to examine the effect of the molar ratio of the divalent cationic metal of the multicomponent bismuth molybdate catalyst, the divalent cationic metal component is added at various molar ratios to the multicomponent bismuth molybdate catalyst composed of three metal components in which the molar ratio of iron:bismuth:molybdenum is fixed to 3:1:12, and thus the activity of the catalyst for the oxidative dehydrogenation of n-butene is determined depending on changes in the molar ratio of the divalent cationic metal in the catalyst. Examples of the divalent cationic metal include any metals which are typically used in the art. To systematically determine the effect of the divalent cationic metal on the activity of the catalyst of the present invention, nickel is used as the divalent cationic metal in the present invention. As a result of experimental reactions, the molar ratio of nickel: iron:bismuth:molybdenum is adjusted to 7~10:3:1:12, and preferably 9:3:1:12 (FIG. 2).

Figure 3:
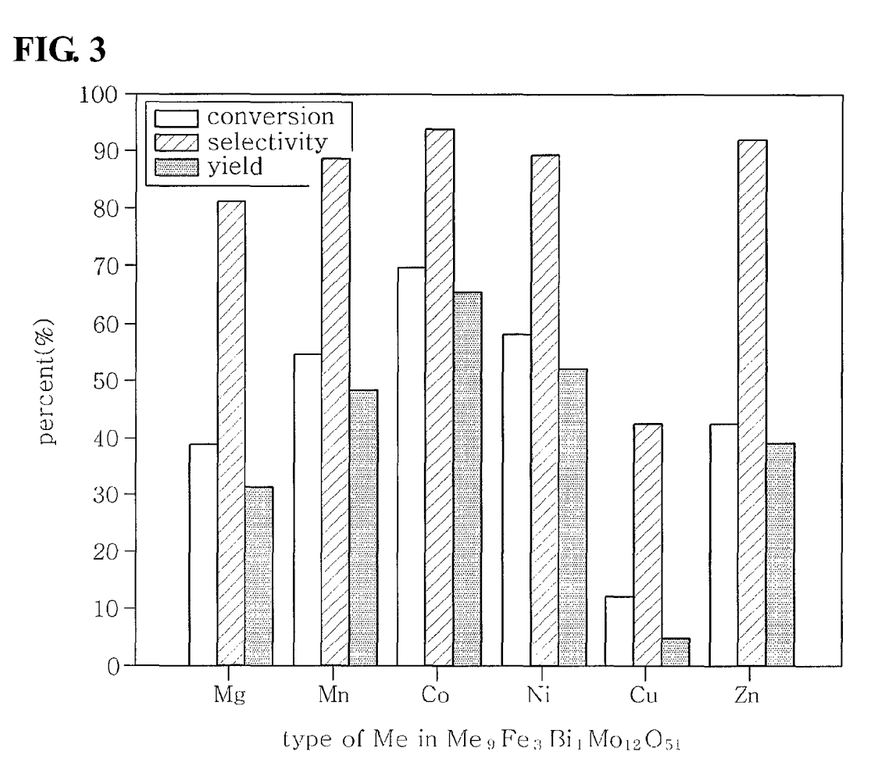
FIG. 3 is a graph showing the reaction activity of six multicomponent bismuth molybdate catalysts composed of four metal components depending on changes in the type of divalent cationic metal (Me), according to Example 3 of the present invention.

In addition, to examine the effect of the type of the divalent cationic metal of the multicomponent bismuth molybdate catalyst on the activity of the catalyst for the oxidative dehydrogenation of n-butene, a multicomponent bismuth molybdate catalyst composed of four metal components is prepared using various divalent cationic metals. As is apparent from the above experimental result, the molar ratio of divalent cationic metal:iron:bismuth:molybdenum is fixed to 9:3:1:12 to prepare a catalyst having high activity for the inventive reaction. Also, as the divalent cationic metal, magnesium, manganese, cobalt, nickel, copper, and zinc are used, thus preparing various multicomponent bismuth molybdate catalysts composed of four metal components. As a result of experimental reactions, metal, manganese, cobalt and nickel are confirmed to be useful as the divalent cation, and in particular, cobalt can be confirmed to be the most useful (FIG. 3).

According to the present invention, the oxidative dehydrogenation of n-butene over the multicomponent bismuth molybdate catalyst occurs in a manner such that n-butene serving as a reactant is adsorbed on the catalyst, and then a lattice oxygen of the catalyst reacts with two hydrogens of adsorbed n-butene, thus producing 1,3-butadiene and water, after which the lattice oxygen vacancy of the catalyst is occupied with molecular oxygen, which is the reactant. In this way, when n-butene is adsorbed on the catalyst, the site of the catalyst able to activate n-butene and the lattice oxygen properties of the catalyst influence the reaction activity. Further, because multicomponent bismuth molybdate catalysts prepared using different types and ratios of metal components have different catalyst phases and ratios and different lattice oxygen properties, various multicomponent bismuth molybdate catalysts composed of four metal components exhibit different activities.

According to the examples of the present invention, the activity of the multicomponent bismuth molybdate catalysts composed of four metal components is seen to vary depending on the types and molar ratios of metal components. Specifically, it is possible to prepare multicomponent bismuth molybdate catalysts composed of four metal components showing high activity for the inventive reaction merely through the appropriate selection of the types of metal components and the adjustment of the molar ratios thereof.

Hence, the catalyst for the production of 1,3-butadiene according to the present invention is a multicomponent bismuth molybdate catalyst composed exclusively of four metal components. Taking into consideration the activity of the catalyst, the multicomponent bismuth molybdate catalyst composed of four metal components is prepared at the molar ratio of divalent cationic metal:trivalent cationic metal:bismuth:molybdenum of 7~10:2~4:1~10:5~20, and preferably 9:3:1:12. As for the catalyst, an example of the trivalent cationic metal includes iron, and examples of the divalent cationic metal include manganese, cobalt, and nickel, in particular, cobalt.

In addition, the present invention provides a method of preparing 1,3-butadiene through the oxidative dehydrogenation over the multicomponent bismuth molybdate catalyst composed of four metal components, using as an n-butene source a C4 mixture or C4 raffinate-3 having high n-butane content, which has not been subjected to additional processes for removing n-butane and separating n-butene.

In the experimental example of the present invention, the catalyst is fixed in a straight type Pyrex reactor, after which the reactor is mounted in an electrical furnace so that the reaction temperature is maintained uniform. The reaction is conducted while the reactant is continuously passed through the catalyst bed of the reactor. The reaction temperature is set to 300~600° C., preferably 350~500° C., and more preferably 420° C. Further, the amount of the catalyst is set such that GHSV (Gas Hourly Space Velocity) is 50~5000 $h^{-1}$, preferably 100~1000 $h^{-1}$, and more preferably 150~500 $h^{-1}$, on the basis of n-butene. The reactants include the C4 mixture, air, and steam, and the ratio of n-butene:air:steam, which are to be introduced into the reactor, is set to 1:0.5~10:1~50, and preferably 1:3~4:10~30. In the case where the volume ratio of the gas mixture is above or below the range of air (0.5~10) or steam (1~50) on the basis of n-butene, the desired yield of butadiene cannot be obtained and/or safety problems may occur following drastic heating during the operation of the reactor.

In the present invention, the amounts of C4 mixture or C4 raffinate-3 used as the n-butene source and of air as another reactant are precisely controlled using a mass flow controller. Water in a liquid phase is evaporated while being introduced using a syringe pump, so that steam is fed into the reactor. The temperature of the portion of the reactor where water in a liquid phase is introduced is maintained at 150~300° C., and preferably 180~250° C., so that water introduced by the syringe pump is instantly evaporated into steam, which is then completely mixed with the other reactants (C4 mixture and air), after which the mixture thus obtained is passed through the catalyst bed of the reactor.

Among the reactants which are reacted over the catalyst of the present invention, the C4 mixture includes 0.5~50 wt % of n-butane, 40~99 wt % of n-butene, and 0.5~10 wt % of other C4 compounds. The other C4 compounds include, for example, isobutane, cyclobutane, methylcyclopropane, and isobutene.

When the multicomponent bismuth molybdate catalyst composed of four metal components according to the present invention is used, 1,3-butadiene can be produced at high yield through the oxidative dehydrogenation of n-butene using the inexpensive C4 mixture or C4 raffinate-3 including n-butane and n-butene as the reactant. In particular, even when the C4 mixture having high n-butane content of at least 20 wt % is directly used as the reactant without using an additional process for removing the n-butane, high conversion of n-butene and high selectivity for 1,3-butadiene can result.

Moreover, the present invention overcomes limitations of conventional techniques including a complicated catalyst synthesis route and difficulties in ensuring reproducibility of catalyst preparation, the problems arising because conventional multicomponent bismuth molybdate catalysts have a very complicated composition of many metal components in order to increase their activity for the oxidative dehydrogenation of n-butene. Further, in the present invention, it is possible to prepare multicomponent bismuth molybdate catalysts having a simple composition of four metal components showing high activity for the inventive reaction as shown through systematic investigation of the types and molar ratios of metal components, thus ensuring reproducibility of catalyst preparation. Furthermore, even when the C4 mixture or C4 raffinate-3 containing many impurities is used as the reactant, 1,3-butadiene can be obtained at high yield, and thus the present technique can be directly applied to a commercial process without the need for an additional process for separating the reactant.

MODE FOR INVENTION

A better understanding of the present invention may be obtained through the following preparative examples, experimental example and examples, which are set forth to illustrate, but are not to be construed to limit the present invention.

Selection of Metal Precursors and Solvents for Preparation of Multicomponent Bismuth Molybdate Catalysts The precursors of magnesium, manganese, cobalt, nickel, copper, and zinc used as a divalent cationic metal were respectively magnesium nitrate hexahydrate ($Mg(NO_3)_2 \cdot 6H_2O$), manganese nitrate hexahydrate ($Mn(NO_3)_2 \cdot 6H_2O$), cobalt nitrate hexahydrate ($Co(NO_3)_2 \cdot 6H_2O$), nickel nitrate hexahydrate ($Ni(NO_3)_2 \cdot 6H_2O$), copper nitrate trihydrate ($Cu(NO_3)_2 \cdot 3H_2O$), and zinc nitrate hexahydrate ($Zn(NO_3)_2 \cdot 6H_2O$) were used. Further, the precursor of iron used as a trivalent cationic metal was ferric nitrate nonahydrate ($Fe(NO_3)_3 \cdot 9H_2O$), and a bismuth precursor and a molybdenum precursor were respectively bismuth nitrate pentahydrate ($Bi(NO_3)_2 \cdot 5H_2O$) and ammonium molybdate tetrahydrate ($(NH_4)_6Mo_7O_{24} \cdot 4H_2O$). Among these precursors, metal precursors with the exception of bismuth nitrate pentahydrate were well dissolved in distilled water, whereas bismuth nitrate pentahydrate, which is dissolved well in a strong acid solution, was separately dissolved in distilled water acidified with nitric acid.

Preparative Example 1

Preparation of Multicomponent Bismuth Molybdate Catalysts Composed of Three Metal Components Specifically, in order to prepare multicomponent bismuth molybdate catalysts composed of three metal components with various iron contents, the molar ratio of bismuth:molybdenum was fixed to 1:12, and the molar ratio of iron:bismuth:molybdenum was changed in the range of 1~4:1:12, thus preparing four catalysts. The amount of ferric nitrate nonahydrate ($Fe(NO_3)_3 \cdot 9H_2O$) corresponding to the molar ratio of iron in each catalyst was determined, dissolved in distilled water (50 ml), and stirred. Separately, 1.47 g of bismuth nitrate pentahydrate ($Bi(NO_3)_2 \cdot 5H_2O$) was dissolved by stirring in distilled water (15 ml) acidified with 3 ml of nitric acid. After the complete dissolution of bismuth, the bismuth solution was added to the solution in which the iron precursor was dissolved, thus preparing an acid solution in which the iron and bismuth precursors were dissolved. Further, 6.36 g of ammonium molybdate tetrahydrate ($(NH_4)_6Mo_7O_{24} \cdot 4H_2O$) was dissolved in distilled water (100 ml) and stirred, and thus the solution thereof was separately prepared. The acid solution in which the iron and bismuth precursors were dissolved was added in droplets to the molybdate solution. The mixture solution thus produced was stirred at room temperature for 1 hour using a magnetic stirrer, after which the precipitated solution was subjected to vacuum concentration or centrifugation, thus obtaining a solid sample. The solid sample thus obtained was dried at 175° C. for 24 hours. The produced solid catalyst was placed in an electrical furnace and thermally treated at 475° C., thereby preparing multicomponent bismuth molybdate catalysts composed of three metal components. The prepared catalysts were subjected to elemental analysis (ICP-AES), whereby the amounts of desired metal precursors were analyzed as being accurately coprecipitated within the error range. The results are shown in Table 1 below.

TABLE 1

Element Ratio of Catalysts of Preparative Example 1

| Catalyst | Fe | Bi | Mo |
|---|---|---|---|
| $Fe_1Bi_1Mo_{12}O_{39}$ | 1.0 | 1.0 | 11.5 |
| $Fe_2Bi_1Mo_{12}O_{40.5}$ | 2.0 | 1.0 | 11.3 |
| $Fe_3Bi_1Mo_{12}O_{42}$ | 3.0 | 1.0 | 11.4 |
| $Fe_4Bi_1Mo_{12}O_{43.5}$ | 4.0 | 1.0 | 11.4 |

Preparative Example 2

Preparation of Multicomponent Bismuth Molybdate Catalysts Composed of Four Metal Components at Different Divalent Cationic Metal Contents In order to prepare multicomponent bismuth molybdate catalysts composed of four metal components at different divalent cationic metal contents, as the divalent cationic metal was used nickel, the molar ratio of iron:bismuth:molybdenum was fixed to 3:1:12, and seven catalysts were prepared in the range of the molar ratio of nickel:iron:bismuth:molybdenum of 2~10:3:1:12. The amount of nickel nitrate hexahydrate ($Ni(NO_3)_2 \cdot 6H_2O$) corresponding to the molar ratio of nickel in each catalyst and 3.66 g of ferric nitrate nonahydrate (Fe$(NO_3)_3 \cdot 9H_2O$) were dissolved in distilled water (50 ml) and stirred. Separately, 1.47 g of bismuth nitrate pentahydrate ($Bi(NO_3)_2 \cdot 5H_2O$) was dissolved by stirring in distilled water (15 ml) acidified with 3 ml of nitric acid. After the complete dissolution of bismuth, the bismuth solution was added to the solution in which the nickel and iron precursors were dissolved, thus preparing an acid solution in which the nickel, iron and bismuth precursors were dissolved. Further, 6.36 g of ammonium molybdate tetrahydrate ($(NH_4)_6Mo_7O_{24} \cdot 4H_2O$) was dissolved in distilled water (100 ml) and stirred, and thus the solution thereof was separately prepared. The acid solution in which the nickel, iron and bismuth precursors were dissolved was added in droplets to the molybdate solution. The mixture solution thus produced was stirred at room temperature for 1 hour using a magnetic stirrer, after which the precipitated solution was subjected to vacuum concentration or centrifugation, thus obtaining a solid sample. The solid sample thus obtained was dried at 175° C. for 24 hours. The produced solid catalyst was placed in an electrical furnace and thermally treated at 475° C., thereby preparing multicomponent bismuth molybdate catalysts respectively composed of four metal components. The prepared catalysts were subjected to element analysis (ICP-AES), whereby the amounts of desired metal precursors were analyzed as being accurately coprecipitated within the error range. The results are shown in Table 2 below.

TABLE 2

Element Ratio of Catalysts of Preparative Example 2

| Catalysts | Ni | Fe | Bi | Mo |
|---|---|---|---|---|
| $Ni_2Fe_3Bi_1Mo_{12}O_{44}$ | 2.0 | 3.0 | 1.0 | 11.5 |
| $Ni_4Fe_3Bi_1Mo_{12}O_{46}$ | 4.1 | 3.0 | 1.0 | 11.5 |
| $Ni_6Fe_3Bi_1Mo_{12}O_{48}$ | 6.0 | 3.0 | 1.0 | 11.3 |
| $Ni_7Fe_3Bi_1Mo_{12}O_{49}$ | 6.8 | 3.0 | 1.0 | 11.7 |
| $Ni_8Fe_3Bi_1Mo_{12}O_{50}$ | 7.9 | 3.2 | 1.0 | 12.6 |
| $Ni_9Fe_3Bi_1Mo_{12}O_{51}$ | 8.7 | 3.2 | 1.0 | 12.0 |
| $Ni_{10}Fe_3Bi_1Mo_{12}O_{52}$ | 9.9 | 3.2 | 1.0 | 12.0 |

Preparative Example 3

Preparation of Multicomponent Bismuth Molybdate Catalysts Composed of Four Metal Components using Various Divalent Cationic Metals In order to prepare multicomponent bismuth molybdate catalysts respectively composed of four metal components using various divalent cationic metals, as the divalent cationic metal, magnesium, manganese, cobalt, nickel, copper, and zinc were used. The molar ratio of divalent cationic metal:iron:bismuth:molybdenum was fixed to 9:3:1:12, and the types of divalent cationic metal were changed, thus preparing six catalysts. Specifically, to prepare a multicomponent bismuth molybdate catalyst composed of four metal components using magnesium, 6.99 g of magnesium nitrate hexahydrate ($Mg(NO_3)_2 \cdot 6H_2O$) and 3.66 g of ferric nitrate nonahydrate ($Fe(NO_3)_3 \cdot 9H_2O$) were dissolved in distilled water (50 ml) and stirred. Separately, 1.47 g of bismuth nitrate pentahydrate ($Bi(NO_3)_2 \cdot 5H_2O$) was dissolved by stirring in distilled water (15 ml) acidified with 3 ml, of nitric acid. After the complete dissolution of bismuth, the bismuth solution was added to the solution in which the nickel and iron precursors were dissolved, thus preparing an acid solution in which the nickel, iron and bismuth precursors were dissolved. Further, 6.36 g of ammonium molybdate tetrahydrate ($(NH_4)_6Mo_7O_{24} \cdot 4H_2O$) was dissolved in distilled water (100 ml) and stirred, and thus the solution thereof was separately prepared. The acid solution in which the nickel, iron and bismuth precursors were dissolved was added in droplets to the molybdate solution. The mixture solution thus produced was stirred at room temperature for 1 hour using a magnetic stirrer, after which the precipitated solution was subjected to vacuum concentration or centrifugation, thus obtaining a solid sample. The solid sample thus obtained was dried at 175° C. for 24 hours. The produced solid catalyst was placed in an electrical furnace and thermally treated at 475° C., thereby preparing a multicomponent bismuth molybdate catalyst composed of four metal components. Also, to prepare multicomponent bismuth molybdate catalysts composed of four metal components using manganese, cobalt, nickel, copper and zinc as the divalent cationic metal, 7.83 g of manganese nitrate hexahydrate ($Mn(NO_3)_2 \cdot 6H_2O$), 7.92 g of cobalt nitrate hexahydrate (Co$(NO_3)_2 \cdot 6H_2O$), 7.93 g of nickel nitrate hexahydrate ($N(NO_3)_2 \cdot 6H_2O$), 6.59 g of copper nitrate trihydrate (Cu$(NO_3)_2 \cdot 3H_2O$), and 8.11 g of zinc nitrate hexahydrate (Zn$(NO_3)_2 \cdot 6H_2O$) were respectively used, and the same subsequent catalyst preparation procedure as the procedure for preparing the multicomponent bismuth molybdate catalyst composed of four metal components using magnesium was conducted.

The catalysts thus prepared were subjected to elemental analysis (ICP-AES), whereby the amounts of desired metal precursors were analyzed as being accurately coprecipitated within the error range. The results are shown in Table 3 below.

TABLE 3

Element Ratio of Catalysts of Preparative Example 3

| Catalysts | Divalent Cationic Metal | Fe | Bi | Mo |
|---|---|---|---|---|
| $Mg_9Fe_3Bi_1Mo_{12}O_{51}$ | 8.7 (Mg) | 3.0 | 1.0 | 11.5 |
| $Mn_9Fe_3Bi_1Mo_{12}O_{51}$ | 9.1 (Mn) | 3.1 | 1.0 | 11.3 |
| $Co_9Fe_3Bi_1Mo_{12}O_{51}$ | 9.0 (Co) | 3.2 | 1.0 | 11.4 |
| $Ni_9Fe_3Bi_1Mo_{12}O_{51}$ | 8.7 (Ni) | 3.2 | 1.0 | 12.0 |
| $Cu_9Fe_3Bi_1Mo_{12}O_{51}$ | 8.8 (Cu) | 2.8 | 1.0 | 11.8 |
| $Zn_9Fe_3Bi_1Mo_{12}O_{51}$ | 8.6 (Zn) | 3.1 | 1.0 | 12.0 |

Experimental Example 1

Oxidative Dehydrogenation of C4 Raffinate-3 or C4 Mixture over Multicomponent Bismuth Molybdate Catalyst Using the multicomponent bismuth molybdate catalysts prepared in Preparative Examples 1, 2 and 3, the oxidative dehydrogenation of n-butene was conducted. As reactants, a C4 mixture, air and steam were used, and a straight type Pyrex reactor was used. The composition of the C4 mixture used as the reactant is shown in Table 4 below. The introduction rate of the reactants was set such that the ratio of n-butene:air:steam was 1:3.75:15. The reaction device was designed such that steam was introduced in the form of water to the inlet of the reactor, specifically, water was directly evaporated into steam at 200° C., mixed with the other reactants, that is, the C4 mixture and air, and then introduced into the reactor. The amounts of C4 mixture and air were controlled using a mass flow controller, and the amount of steam was controlled by adjusting the speed of a syringe pump filled with water. The amount of the catalyst was set so that GHSV was 475 $h^{-1}$ on the basis of n-butene in the C4 mixture, and the reaction temperature was maintained so that the temperature of the catalyst bed was 420° C., and under these conditions the reaction was conducted. Thereafter, the reaction product was analyzed using gas chromatography. The product was composed of carbon dioxide resulting from complete oxidation, cracking by-products, and n-butane, in addition to desired 1,3-butadiene. Through the oxidative dehydrogenation of n-butene over the multicomponent bismuth molybdate catalyst, the conversion of n-butene, the selectivity of 1,3-butadiene, and the yield of 1,3-butadiene were respectively calculated from Equations 1, 2, and 3 below.

$$\text{Conversion (\%)} = \frac{\text{number of moles of } n-\text{butene reacted}}{\text{number of moles of } n-\text{butene fed}} \times 100 \quad \text{Equation 1}$$

$$\text{Selectivity (\%)} = \frac{\text{number of moles of } 1,3-\text{butadiene produced}}{\text{number of moles of } n-\text{butene reacted}} \times 100 \quad \text{Equation 2}$$

$$\text{Yield (\%)} = \frac{\text{number of moles of } 1,3-\text{butadiene produced}}{\text{number of moles of } n-\text{butene fed}} \times 100 \quad \text{Equation 3}$$

TABLE 4

Composition of C4 Mixture as Reactant

| Composition | Molecular Formula | Mass % |
|---|---|---|
| Iso-butane | $C_4H_{10}$ | 0.07 |
| n-Butane | $C_4H_{10}$ | 41.57 |
| Methyl Cyclopropane | $C_4H_8$ | 0.09 |
| Trans-2-butene | $C_4H_8$ | 33.94 |
| 1-Butene | $C_4H_8$ | 7.52 |
| Isobutylene | $C_4H_8$ | 0.02 |
| Cis-2-butene | $C_4H_8$ | 16.48 |
| Cyclopropane | $C_3H_6$ | 0.29 |
| Iso-pentane | $C_5H_{12}$ | 0.02 |
| Total | | 100 |

Example 1

Reaction Activity of Multicomponent Bismuth Molybdate Catalysts Composed of Three Metal Components with Different Iron Contents The oxidative dehydrogenation of the C4 mixture was conducted according to the process of Experimental Example 1 using the multicomponent bismuth molybdate catalysts composed of three metal components with different iron contents of Preparative Example 1. The results are shown in Table 5 below. As the iron content was changed, the formed catalysts had different catalyst phases and ratios and accordingly the surface properties and lattice oxygen properties thereof were varied, resulting in different activities. Further, the effect of the iron content on the activity of the catalyst is depicted in FIG. 1. The yield of 1,3-butadiene was represented by a volcano curve depending on the changes in the iron content, and the greatest activity was exhibited at a molar ratio of iron:bismuth:molybdenum of 3:1:12. Therefore, in the preparation of multicomponent bismuth molybdate catalysts composed of four metal components as mentioned below, the molar ratio of iron:bismuth:molybdenum was fixed to 3:1:12.

TABLE 5

Reaction Activity of Multicomponent Bismuth Molybdate Catalysts composed of Three Metal Components with Different Iron Contents

| Catalysts | n-Butene Conversion (%) | 1,3-Butadiene Selectivity (%) | 1,3-Butadiene Yield (%) |
|---|---|---|---|
| $Fe_1Bi_1Mo_{12}O_{39}$ | 14.7 | 75.2 | 11.1 |
| $Fe_2Bi_1Mo_{12}O_{40.5}$ | 35.6 | 77.0 | 27.4 |
| $Fe_3Bi_1Mo_{12}O_{42}$ | 45.1 | 85.8 | 38.7 |
| $Fe_4Bi_1Mo_{12}O_{43.5}$ | 29.6 | 71.7 | 21.2 |

Example 2

Reaction Activity of Multicomponent Bismuth Molybdate Catalysts Composed of Four Metal Components with Different Nickel Contents The oxidative dehydrogenation of the C4 mixture was conducted according to the process of Experimental Example 1 using the multicomponent bismuth molybdate catalysts composed of four metal components with different nickel contents of Preparative Example 2. The results are shown in Table 6 below. As the nickel content was changed, the formed catalysts had different catalyst phases and ratios and accordingly the surface properties and lattice oxygen properties thereof were varied, resulting in different activities. Further, the effect of the nickel content on the activity of the catalyst is shown in FIG. 2. The yield of 1,3-butadiene was represented by a volcano curve depending on the changes in the nickel content, and the greatest activity was exhibited at a molar ratio of nickel:iron:bismuth:molybdenum of 9:3:1:12. Therefore, in the preparation of multicomponent bismuth molybdate catalysts composed of four metal components using various divalent cationic metals, with the exception of nickel, the molar ratio of divalent cationic metal:iron:bismuth:molybdenum was fixed to 9:3:1:12.

TABLE 6

Reaction Activity of Multicomponent Bismuth Molybdate Catalysts composed of Four Metal Components with Different Nickel Contents

| Catalysts | n-Butene Conversion (%) | 1,3-Butadiene Selectivity (%) | 1,3-Butadiene Yield (%) |
|---|---|---|---|
| $Ni_2Fe_3Bi_1Mo_{12}O_{44}$ | 45.9 | 84.3 | 38.7 |
| $Ni_4Fe_3Bi_1Mo_{12}O_{46}$ | 45.5 | 84.6 | 38.5 |
| $Ni_6Fe_3Bi_1Mo_{12}O_{48}$ | 46.4 | 84.9 | 39.4 |
| $Ni_7Fe_3Bi_1Mo_{12}O_{49}$ | 47.0 | 84.6 | 39.8 |
| $Ni_8Fe_3Bi_1Mo_{12}O_{50}$ | 51.4 | 85.2 | 43.7 |
| $Ni_9Fe_3Bi_1Mo_{12}O_{51}$ | 58.8 | 89.7 | 52.7 |
| $Ni_{10}Fe_3Bi_1Mo_{12}O_{52}$ | 50.4 | 87.4 | 44.0 |

Example 3

Reaction Activity of Multicomponent Bismuth Molybdate Catalysts Composed of Four Metal Components with Various Divalent Cationic Metals The oxidative dehydrogenation of the C4 mixture was conducted according to the process of Experimental Example 1 using the multicomponent bismuth molybdate catalysts composed of four metal components with various divalent cationic metals of Preparative Example 3. The results are shown in Table 7 below. As the type of divalent cationic metal was changed, the formed catalysts had different catalyst phases and accordingly the surface properties and lattice oxygen properties thereof were varied, resulting in different activities. Further, the effect of the type of divalent cationic metal on the activity of the catalyst is shown in FIG. 3. When manganese, cobalt and nickel were used as the divalent cationic metal, higher yield of 1,3-butadiene was obtained. Particularly, the use of cobalt as the divalent cationic metal resulted in the highest yield of 1,3-butadiene.

TABLE 7

Reaction Activity of Multicomponent Bismuth Molybdate Catalysts composed of Four Metal Components with Various Divalent Cationic Metals

| Catalysts | n-Butene Conversion (%) | 1,3-Butadiene Selectivity (%) | 1,3-Butadiene Yield (%) |
|---|---|---|---|
| $Mg_9Fe_3Bi_1Mo_{12}O_{51}$ | 39.0 | 81.4 | 31.8 |
| $Mn_9Fe_3Bi_1Mo_{12}O_{51}$ | 54.7 | 88.8 | 48.6 |
| $Co_9Fe_3Bi_1Mo_{12}O_{51}$ | 70.1 | 94.4 | 66.2 |
| $Ni_9Fe_3Bi_1Mo_{12}O_{51}$ | 58.8 | 89.7 | 52.7 |
| $Cu_9Fe_3Bi_1Mo_{12}O_{51}$ | 12.6 | 42.9 | 5.4 |
| $Zn_9Fe_3Bi_1Mo_{12}O_{51}$ | 42.9 | 92.5 | 39.7 |

The invention claimed is:

1. A method of preparing a multicomponent bismuth molybdate catalyst, comprising:
    a) preparing a first solution including a precursor of a trivalent cationic metal including iron, a precursor of a divalent cationic metal selected from the group consisting of magnesium, manganese, cobalt, nickel, copper, zinc, and a bismuth precursor;
    b) preparing a second solution, in which a molybdenum precursor is dissolved;
    c) adding the first solution in droplets to the second solution so that coprecipitation occurs, thus obtaining a coprecipitated solution;
    d) subjecting the coprecipitated solution to stirring for about 1 to about 2 hours and then dewatering, thus obtaining a solid component; and
    e) subjecting the solid component to drying at 150-200° C. and then thermal treatment at 400-600° C.,
    wherein the multibismuth molybdate catalyst consists of four (4) metal components of the trivalent cationic metal, the divalent cationic metal, bismuth and molybdenum; and
    wherein a molar ratio of the precursor of the divalent cationic metal:the precursor of the trivalent cationic metal:bismuth precursor:molybdenum precursor is about 7 to about 10:2-4:1:5-20.

2. The method according to claim 1, wherein a molar ratio of the precursor of the divalent cationic metal:the precursor of the trivalent cationic metal:bismuth precursor:molybdenum precursor is 9:3:1:12.

3. A method of preparing 1,3-butadiene, comprising:
    a) packing a reactor with a fixed bed of the bismuth molybdate catalyst prepared according to claim 1;
    b) performing oxidative dehydrogenation while continuously passing reactants comprising a C4 mixture including n-butene, air, and steam through the catalyst bed of the reactor; and
    c) obtaining 1,3-butadiene.

4. The method according to claim 3, wherein the reactants are composed of n-butene, air and steam in a molar ratio of 1:about 0.5 to about 10:about 1 to about 50.

5. The method according to claim 3, wherein the oxidative dehydrogenation is performed at a reaction temperature of 300-600° C. and a gas hourly space velocity of about 50 to about 5000 $h^{-1}$ on the basis of n-butene.

6. A method of preparing 1,3-butadiene, comprising:
    a) packing a reactor with a fixed bed of the bismuth molybdate catalyst prepared according to claim 2;
    b) performing oxidative dehydrogenation while continuously passing reactants comprising a C4 mixture including n-butene, air, and steam through the catalyst bed of the reactor; and
    c) obtaining 1,3-butadiene.

7. The method according to claim 6, wherein the reactants are composed of n-butene, air and steam in a molar ratio of 1:about 0.5 to about 10:about 1 to about 50.

8. The method according to claim 6, wherein the oxidative dehydrogenation is performed at a reaction temperature of 300-600° C. and a gas hourly space velocity of about 50 to about 5000 $h^{-1}$ on the basis of n-butene.

* * * * *